United States Patent
Henry et al.

(10) Patent No.: US 10,028,896 B2
(45) Date of Patent: Jul. 24, 2018

(54) SKIN TREATMENT COMPOSITION

(71) Applicant: 3M INNOVATIVE PROPERTIES COMPANY, Saint Paul, MN (US)

(72) Inventors: Andrew R. Henry, Leicestershire (GB); Matthew Hurley, Nottinghamshire (GB); Colum Dwyer, Nottinghamshire (GB)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/312,108

(22) PCT Filed: Jun. 9, 2015

(86) PCT No.: PCT/US2015/034780
§ 371 (c)(1),
(2) Date: Nov. 17, 2016

(87) PCT Pub. No.: WO2015/199966
PCT Pub. Date: Dec. 30, 2015

(65) Prior Publication Data
US 2017/0100311 A1    Apr. 13, 2017

Related U.S. Application Data

(60) Provisional application No. 62/017,540, filed on Jun. 26, 2014.

(51) Int. Cl.
| | |
|---|---|
| *A61K 8/06* | (2006.01) |
| *A61K 8/31* | (2006.01) |
| *A61K 8/37* | (2006.01) |
| *A61K 8/81* | (2006.01) |
| *A61K 8/891* | (2006.01) |
| *A61Q 17/00* | (2006.01) |
| *A61K 8/86* | (2006.01) |
| *A61K 8/92* | (2006.01) |

(52) U.S. Cl.
CPC .............. *A61K 8/064* (2013.01); *A61K 8/31* (2013.01); *A61K 8/37* (2013.01); *A61K 8/8152* (2013.01); *A61K 8/86* (2013.01); *A61K 8/891* (2013.01); *A61K 8/922* (2013.01); *A61Q 17/00* (2013.01)

(58) Field of Classification Search
CPC . A61K 8/064; A61K 8/31; A61K 8/37; A61K 8/8152; A61K 8/86
See application file for complete search history.

(56) References Cited

U.S. PATENT DOCUMENTS

| | | | |
|---|---|---|---|
| 3,538,914 A | 11/1970 | Myers | |
| 3,845,769 A | 11/1974 | Shaw | |
| 4,552,755 A * | 11/1985 | Randen | A61K 8/062 424/744 |
| 5,254,122 A | 10/1993 | Shaw | |
| 6,152,893 A | 11/2000 | Pigg | |
| 2003/0171479 A1* | 9/2003 | Lennon | A61K 8/06 524/501 |
| 2005/0192524 A1 | 9/2005 | Lipshaw | |
| 2005/0209545 A1 | 9/2005 | Farrow | |
| 2007/0179421 A1 | 8/2007 | Farrow | |
| 2013/0319128 A1 | 12/2013 | Richardson | |

FOREIGN PATENT DOCUMENTS

| | | |
|---|---|---|
| EP | 1974704 | 10/2008 |
| GB | 2473321 | 3/2011 |
| WO | WO 1997-46181 | 12/1997 |
| WO | WO 2001-72250 | 10/2001 |
| WO | WO 2006-110527 | 10/2006 |
| WO | WO 2007-065435 | 6/2007 |
| WO | WO 2010-117723 | 10/2010 |
| WO | WO 2011-066237 | 6/2011 |
| WO | WO 2014-116497 | 7/2014 |
| WO | WO 2014-132127 | 9/2014 |
| WO | WO 2014-160572 | 10/2014 |
| WO | WO 2016-003790 | 1/2016 |

OTHER PUBLICATIONS

Merriam-Webster Dictionary (accessed on Sep. 24, 2017, pp. 1-2, https://www.merriam-webster.com/dictionary/flake).*
PPG 15 stearyl ether definition (https://www.ewg.org/skindeep/ingredient/722835/PPG-5_STEARYL_ETHER/#.WwNLgjbrufA, EWG's Skin Deep Cosmetics Database, 3 pages, Accessed on May 21, 2018).*
Dissolve definition (https://www.merriam-webster.com/dictionary/dissolve, Merriam-Webster Dictionary, Accessed May 21, 2018, 1 page).*
International Search Report for PCT International Application No. PCT/US2015/050945, dated Dec. 4, 2015, 5pgs.

* cited by examiner

*Primary Examiner* — Alma Pipic
(74) *Attorney, Agent, or Firm* — 3M Innovative Properties Company; Lynn R. Hunsberger

(57) ABSTRACT

A composition for application to mammalian skin. The composition can include an emulsion comprising an oil phase. The oil phase can include (a) an acrylate polymer in an amount of from about 0.25 wt % to about 10 wt %, and (b) a silicone resin in an amount of from about 0.5 wt % to about 15 wt %; wherein (a) and (b) are dissolved in a non-volatile emollient oil.

19 Claims, No Drawings

SKIN TREATMENT COMPOSITION

CROSS REFERENCE TO RELATED APPLICATIONS

This application is a national stage filing under 35 U.S.C. 371 of PCT/US2015/034780, filed Jun. 9, 2015, which claims the benefit of U.S. Provisional Application No. 62/017,540, filed Jun. 26, 2014, the disclosures of which are incorporated by reference in their entirety herein.

FIELD

The present disclosure generally relates to a composition for application to mammalian skin.

BACKGROUND

Skin breakdown is a common consequence of both urinal and fecal incontinence, leading to Incontinence Associated Dermatitis (IAD). Early stage IAD is categorized by erythema and reddening of at-risk skin and in more serious cases, can involve denudation and skin breakdown.

The effects of alkaline metabolites from urine and/or active enzymes, such as elastase and trypsin in the case of fecal incontinence, can cause breakdown of skin. The effective treatment of IAD can include the mitigation of "risk" factors, including effective management of the incontinence and protection of at-risk skin areas.

Treatment of IAD can also include cleaning with a soap and wipe material, followed by the use of a skin moisturizing and protection product. This skin moisturization and protection is offered by a range of commercially available skin conditioning formulations, typically containing emollient oils, humectants and skin protectant ingredients.

Some commercially available moisturizing lotions and ointments commonly used to treat Incontinence Associated Dermatitis (IAD) and protect mammalian skin consist of oil-in-water emulsions and creams, water-in-oil emulsions, and to a lesser extent 100% oil formulations. Other commercially available products include volatile solvent based film forming products that, after application, deposit a polymeric film onto the skin.

SUMMARY

Many existing products for the treatment of IAD present in the market place have various limitations. For example, some existing products are subject to easy removal and can transfer to bed clothing, linen, or the like. This easy removal can decrease the effectiveness of the product after its application.

Furthermore, some existing oil-in-water emulsion systems are less resilient to being washed off, because water is the continuous phase, and any hydrophobic (film forming) material is held in the discontinuous phase, and therefore not in direct contact with the skin immediately upon application, increasing its likelihood of premature or undesirable wash-off.

In addition, some existing emulsion systems include additional emulsifiers or surfactants to ensure a stable emulsion formation. However, the use of such additional surfactants can be detrimental to the conditioning of the skin offered by a product as such surfactants can strip the skin surface of oils and lipids. In addition, by their nature, any surfactants present in a formulation can facilitate the penetration of any barrier layer formed on the skin surface by moisture and irritants, thereby reducing the barrier effectiveness.

The present disclosure is generally directed to a moisturizing, substantive, durable barrier cream skin treatment composition comprising an emulsion (e.g., a water-in-oil emulsion or an oil-in-water emulsion) that offers a stable formulation without the need for additional emulsifiers or surfactants, and which offers superior performance to formulations containing additional emulsifiers. The skin treatment compositions of the present disclosure provide stable emulsion systems which generally include an oil phase comprising (a) acrylate polymer (e.g., an oil-soluble acrylate polymer) and (b) a silicone resin (e.g., a methylated silicone resin).

In addition, the skin treatment compositions of the present disclosure can (i) provide durability to skin, (ii) reduce the ingress of moisture into the skin, and/or (iii) can enhance (or at least not negatively impact) the adhesion of pressure-sensitive adhesives to skin treated with the composition (e.g., as compared to skin treated with an emollient oil alone).

Some aspects of the present disclosure provide a composition for application to mammalian skin. The composition can include an emulsion comprising an oil phase. The oil phase can include (a) an acrylate polymer in an amount of from about 0.25 wt % to about 10 wt %, and (b) a silicone resin in an amount of from about 0.5 wt % to about 15 wt %; wherein (a) and (b) are dissolved in a non-volatile emollient oil.

Other features and aspects of the present disclosure will become apparent by consideration of the detailed description.

DETAILED DESCRIPTION

The present disclosure generally relates to a skin treatment composition comprising an emulsion (e.g., a water-in-oil emulsion) comprising an oil phase comprising (a) an acrylate polymer and (b) a silicone resin, wherein (a) and (b) are dissolved in a nonvolatile emollient oil, and wherein the composition is essentially free of any additional emulsifiers (i.e., beyond any already listed above). The composition can be configured to dry to a coating comprising at least 60 wt % of the emollient oil.

Definitions

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, n-propenyl, and n-butenyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "aralkyl" refers to a monovalent group of formula —$R^a$—Ar where $R^a$ is an alkylene and Ar is an aryl group. That is, the aralkyl is an alkyl substituted with an aryl.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The terms "room temperature" and "ambient temperature" are used interchangeably to mean a temperature in the range of 20° C. to 25° C.

The phrase "essentially free of any additional emulsifiers" is used to acknowledge that the acrylate polymer may itself have some emulsifying or surfactant properties (e.g., when a monomeric mixture from which the polymer is derived comprises from 10 to 50 mole percent of one or more acid monomers), but the composition does not require additional emulsifiers be added to form a stable emulsion system.

Generally, "essentially free of" a material, substance or ingredient means that the material (e.g., additional emulsifiers, i.e., in addition to the acrylate polymer) was not intentionally added to the composition, such that the composition includes less than 0.5 wt % of the material; in some embodiments, less than 0.3 wt %; in some embodiments, less than 0.2 wt %; in some embodiments, less than 0.1 wt %; in some embodiments, less than 0.05 wt %; in some embodiments, less than 0.01 wt %; in some embodiments, less than 0.001 wt %; and in some embodiments, includes 0.000 wt % of the material.

Skin treatment compositions of the present disclosure are particularly suited for application to non-mucosal and non-oral mammalian skin. Particularly suitable skin treatment emulsion compositions of the present disclosure are in the form of a cream or lotion, i.e., a moisturizing, durable barrier cream.

Water-in-oil emulsions are generally preferred to oil-in-water emulsion systems as barrier formulations because the hydrophobic materials form the continuous phase of a water-in-oil emulsion and are deposited directly on the skin first and therefore form a barrier that is more resistant to wash-off and transfer. This is in contrast to oil-in-water emulsion systems, which generally include additional emulsifiers or surfactants that may weaken barrier properties of the composition.

The destabilizing effects (i.e., unstable emulsion systems) observed in the combination of the commercially available polymers with a silicone resin has been shown to only be stabilized with the addition of an additional emulsifier to the formulation. However, an additional emulsifier is not needed in the compositions of the present disclosure. That is, the compositions of the present disclosure employ an acrylate polymer and a silicone resin, which offer a novel solution to stabilizing an emulsion system, without the use of any additional surfactants or emulsifiers, such that the compositions are essentially free of additional emulsifiers.

The compositions of the present disclosure also do not impact the adhesion of pressure-sensitive adhesives (e.g., in the form of tapes, dressings, etc.) to the skin surface, and can offer a level of water resistance due to the continuous oil phase.

Surprisingly, it is further noted that the combination of an acrylate polymer and a silicone resin provides a stable emulsion that was not observed in the combination of a silicone resin with other commercially available polymers.

In some embodiments, the compositions of the present disclosure can be essentially free of any ethylene acrylic acid copolymers.

Particularly useful compositions of the present disclosure are emulsions in the form of lotions or creams. The emulsions can be of two basic types, i.e., oil-in-water and water-in-oil emulsions, with water-in-oil emulsions found to be particularly useful. The emulsions can be made by first preparing an oil phase by mixing the oil base (e.g., the emollient oil), the acrylate polymer and the silicone resin together and warming the mixture with slow agitation to at least about 70° C. (158° F.), e.g., to about 95° C. (203° F.). The oil phase can include from about 0.25 wt % to about 40 wt % of acrylate polymer, and particularly, from about 3 wt % to about 10 wt % of acrylate polymer. At levels much above 20 wt % of acrylate polymer (i.e., of the oil phase), the resulting composition can become sticky and unpleasant feeling.

As mentioned above, in some embodiments, the compositions of the present disclosure can be formulated into a cream, lotion, or the like. In some embodiments, the compositions of the present disclosure can have a viscosity of at least about 5 Pa·s, in some embodiments, at least 7 Pa·s, and in some embodiments, at least 10 Pa·s. In some embodiments, the compositions of the present disclosure can have a viscosity of no greater than 250 Pa·s, in some embodiments, no greater than 200 Pa·s, and in some embodiments, no greater than 150 Pa·s. Viscosity measurements of a composition can be taken by first allowing a sample to equilibrate at room temperature for about 24 hrs to allow for settling. Then, the viscosity can be measured using a viscometer, such as a viscometer available from Cole Parmer; Spindle Type: L4; RPM: 6.

In some embodiments, compositions (i.e., emulsions) of the present disclosure can include at least about 30 wt % of water; in some embodiments, at least about 35 wt %; in some embodiments, at least about 40 wt %; and in some embodiments, at least about 45 wt %. In some embodiments, compositions (i.e., emulsions) of the present disclosure can include no greater than about 90 wt %; in some embodiments, no greater than about 70 wt %; in some embodiments, no greater than about 60 wt %; and in some embodiments, no greater than about 55 wt %. In some embodiments, compositions (i.e., emulsions) of the present disclosure can include between 35 and 90 wt % of water. In some embodiments, compositions (i.e., emulsions) of the present disclosure can include between 35 and 60 wt % of water. In some embodiments, compositions (i.e., emulsions) of the present disclosure can include between 45 and 55 wt % of water. Although water is used in the emulsions of the present disclosure, the fact that the water evaporates is not an important feature of the compositions of the present disclosure. The film that is left behind on the skin is an oil film identical to the film that is coated out from the oil system. A continuous, dry, polymeric film is not cast on the skin in either case.

The emulsions are generally prepared by heating, independently, the oil phase (i.e., containing the acrylate polymer and silicone resin) and the water phase, and slowly adding the water phase to the oil phase with good agitation. Homogenization can be preferred, but it is not necessary. Humectants may also be incorporated into the water phase. Suitable humectants include, but are not limited to, polyols, such as glycerine, propylene glycol, dipropylene glycol, polypropylene glycol, glycerine ethoxylates, methyl glucose ethoxylates, polyethylene glycol, polyethylene/polypropylene glycols, sorbitol, and α-hydroxy acids (e.g., glycolic acid or the ammonium salt of lactic acid). Dipropylene glycol and polypropylene glycol can be particularly useful as humectants.

In some embodiments, the compositions of the present disclosure can further include low levels of stabilizing ingredients in the water phase. Salts, such as magnesium sulfate, have proven to be useful emulsion stabilizers that do not significantly affect the water resistance of the formulations. In some embodiments, the compositions of the present disclosure can further include one or more water-soluble gums (such as guar derivatives, xanthan gum, and aloe vera) and/or thickeners (such as hydroxy ethyl cellulose, hydroxy methyl cellulose and carboxyl vinyl polymers).

In some embodiments, a silicone oil (dimethicone) can be added to the oil phase prior to preparation of the emulsion, which can improve the ability of the emulsions to act as a barrier to urine, feces or other indigenous and exogenous materials. In some embodiments, dimethicone can be present in concentrations up to 5 wt % of the emulsion. Fragrances, dyes, colorants, preservatives, antioxidants, antimicrobials and other such materials conventionally used in moisturizing compositions may also be included in minor amounts in the compositions without affecting the substantivity of the compositions. In some embodiments, these materials can be added after the emulsions have been prepared and cooled. In some embodiments, these materials can be added while the emulsions are being cooled.

When applied to mammalian skin, compositions of the present disclosure form an oil film on the skin surface. Surprisingly, in spite of the oiliness and moisturizing effects of the compositions, pressure-sensitive adhesives, such as medical tapes, dressings, or the like, adhere at least as well and, in some cases, more strongly to treated skin than to untreated skin. In some embodiments, compositions of the present disclosure can be formulated such that the adhesion of the pressure-sensitive adhesive to the skin coated with the composition is greater than the adhesion of the pressure-sensitive adhesive to skin coated with the emollient oil alone.

Medical tapes which adhere particularly well to the skin that has been treated with a composition of the present disclosure include those utilizing acrylate and rubber-based pressure-sensitive adhesives. Examples include, but are not limited to, tapes available under the trade designations TRANSPORE™, BLENDERM™, STERI-STRIPS™ and MICROPORE™.

Compositions of the present disclosure are water-repellant, moisturizing and long-lasting, compared to other commercially available skin lotions. These features can be particularly useful for ostomy or incontinence applications, where protection of the skin from irritating body fluids such as urine, feces and intestinal fluids is desired. In addition, because the compositions do not negatively impact the adhesion of pressure-sensitive adhesives, the compositions can be used to protect skin surrounding stomas, dermal ulcers, diseased skin or surgical wounds without interfering with the application of adhesive wound dressings.

Compositions of the present disclosure can be "durable" or "substantive," such that the compositions provide a barrier durability (tested as described in the 'Examples' section) of at least 35% after at least two incontinence episodes (or simulated incontinence episodes, as described in the 'Examples' section); in some embodiments, at least 40%; in some embodiments, at least 50%; in some embodiments, at least 60%; in some embodiments, at least 70%; in some embodiments, at least 75%; in some embodiments, at least 80%; in some embodiments, at least 85%; in some embodiments, at least 90%, in some embodiments, at least 95%; and in some embodiments, at least 97%.

Acrylate Polymer

Acrylate polymers of the present disclosure can include copolymers, terpolymers, etc. derived from the polymerization of at least one ester monomer and at least one acid monomer. The ester monomer is selected from the same or different monomers of Formula I:

where:

$R^1$ is an alkyl radical containing 4 to 18 carbon atoms in cyclic, straight- or branched-chain configuration, and $R^2$ is hydrogen or a lower alkyl, where the phrase "lower alkyl" refers to an alkyl radical containing one to four carbon atoms.

The acid monomer is selected from the same or different monomers of Formula II:

where:

$R^3$ is hydrogen (—H) or an alkyl group containing 1 to 18 carbon atoms;

$R^4$ is hydrogen (—H), methyl (—CH$_3$), or —CO$_2$R$^3$, and $R^5$ is hydrogen (—H), a lower alkyl or —CH$_2$CO$_2$R$^3$;

provided that when $R^4$ is not hydrogen, $R^5$ is hydrogen and when $R^5$ is not hydrogen, $R^4$ is hydrogen, and further provided that at least one $R^3$ is hydrogen.

In some embodiments, the acrylate polymer can be prepared using the corresponding alkyl esters of acrylic, methacrylic, itaconic or maleic acid, wherein the ester alkyl groups may contain 1 to 18 carbon atoms and are exemplified by methyl, ethyl, butyl, methylisoamyl, n-hexyl, 2-ethylhexyl, isooctyl, isodecyl, lauryl, octadecyl, stearyl groups, and the like. In some embodiments, the acrylate polymer can include the acrylates and methacrylates with alkyl groups containing 6 to 18 carbon atoms.

Esters wherein the alkyl group contains less than four carbon atoms may be included in small amounts, e.g. less than 10 mole percent. However, generally, in order to achieve a desired solubility parameter, the acrylate polymers should generally not contain a significant amount of lower alkyl ester monomers.

In some embodiments, ester monomers of Formula I can include alkyl esters such as: n-butyl acrylate, n-butyl methacrylate, iso-butyl acrylate, iso-butyl methacrylate, sec-butyl acrylate, sec-butyl methacrylate, n-amyl acrylate, n-amyl methacrylate, iso-amyl acrylate, iso-amyl methacrylate, n-hexyl acrylate, n-hexyl methacrylate, cyclohexyl acrylate, 2-ethylbutyl acrylate, 2-ethylbutyl methacrylate, n-heptyl acrylate, n-heptyl methacrylate, n-octyl acrylate, n-octyl methacrylate, 2-ethylhexyl acrylate, 2-ethylhexyl methacrylate, iso-octyl acrylate, iso-octyl methacrylate, n-nonyl acrylate, n-nonyl methacrylate, n-decyl acrylate, n-decyl methacrylate, iso-decyl acrylate, iso-decyl methacrylate, undecyl methacrylate, lauryl acrylate, lauryl methacrylate, hexadecyl acrylate, hexadecyl methacrylate, octadecyl acrylate, octadecyl methacrylate, stearyl methacrylate, β-carboxyethyl acrylate, and mixtures thereof.

In some embodiments, acid monomers can include the unesterified α,β-olefinically unsaturated carboxylic acids of Formula II, such as acrylic acid, methacrylic acid, maleic acid, itaconic acid, ethacrylic acid and mixtures thereof. The presence of the carboxylic acid monomer generally contributes to the substantivity of the compositions and the ability of adhesives to adhere to skin coated with these compositions.

In some embodiments, the acrylate polymer can be derived from about 5 to 60 mole percent of the acid monomers and about 40 to 95 mole percent of the alkyl ester monomers. In some embodiments, the acrylate polymer can be derived from 10 to 40 mole percent of the olefinically unsaturated carboxylic acid monomers and 60 to 90 mole percent of the alkyl ester monomers containing 4 to 18 carbon atoms in the ester alkyl groups. In some embodiments, the acrylate polymer can be derived from 15 to 30 mole percent of the olefinically unsaturated carboxylic acid monomers and 70 to 85 mole percent of the alkyl ester monomers containing 4 to 18 carbon atoms in the ester alkyl groups.

When difunctional acid monomers only are included along with the ester monomers of Formula I, the mole percent of such acid monomers should generally not exceed about 30 in order to maintain a desired solubility parameter of between 6 and 10 $(cal/cc)^{1/2}$ in poorly hydrogen bonding solvents.

One exemplary acrylate terpolymer is derived from isooctyl acrylate (e.g., at least 50 mole percent, or at least 55 mole percent), stearyl methacrylate (e.g., at least 30 mole percent, or at least 40 mole percent) and acrylic acid (e.g., at least 5 mole percent, at least 10 mole percent, or at least 20 mole percent).

One of ordinary skill in the art will understand how to prepare the polymers from the monomers, which can be carried out by standard bulk, solution or emulsion techniques. Generally, the latter two techniques can be particularly useful, with solution polymerization in an oil being most particularly useful. The polymerization of the monomers can be catalyzed by free radical-generating catalysts such as peroxides, azo catalysts and the like. To be most effective, the reactor for such polymerizations may be purged with an inert gas in order to remove traces of oxygen. The solution polymerizations can be run in a compatible oil solvent such that the final polymer solution contains 10 to 40 percent solids. The working and reference examples in the Examples section below employed 25 percent solids acrylate polymer formulations.

The molecular weight of the acrylate polymers used in the compositions of the present disclosure may vary over a broad range. The molecular weight can be suitably large to provide a desired binding effect between the coating composition and an adhesive applied over the coating composition. The upper limit can be determined largely by formulation requirements. As the molecular weight increases, the polymers can become too viscous to formulate easily into cosmetically appealing compositions.

Generally, acrylate polymers having a Brookfield viscosity (as measured using a viscometer available from Cole Parmer; Spindle Type L4; RPM: 12; 25° C.) between 0.05 and 250 Pa·s, and particularly between 5 and 40 Pa·s, when measured at about 25 percent nonvolatiles (e.g., isopropyl palmitate, or other suitable nonvolatile), can be useful in compositions of the present disclosure. However, the Brookfield viscosity can depend on the nonvolatile employed. Alternatively, the viscosity of acrylate polymers of the present disclosure can be characterized by inherent viscosity (IV). In some embodiments, acrylate polymers of the present disclosure can have an IV of at least 1.2, when measured in tetrahydrofuran (THF) at a concentration of 0.1 g/dL.

In addition, in some embodiments, the acrylate polymers of the present disclosure can have a weight average molecular weight ($M_w$) ranging from about 500,000 ($5 \times 10^5$) g/mol to about 3,000,000 ($3 \times 10^6$) g/mol; in some embodiments, from about 800,000 ($8 \times 10^5$) g/mol to about 2,000,000 ($2 \times 10^6$) g/mol; and in some embodiments, from about 1,000,000 ($1 \times 10^6$) g/mol to about 1,500,000 ($1.5 \times 10^6$) g/mol. In some embodiments, the acrylate polymers of the present disclosure can have a number average molecular weight (MO ranging from about 100,000 ($1 \times 10^5$) g/mol to about 500,000 ($5 \times 10^5$) g/mol; in some embodiments, from about 150,000 ($1.5 \times 10^5$) g/mol to about 400,000 ($4 \times 10^5$) g/mol; and in some embodiments, from about 200,000 ($2 \times 10^5$) g/mol to about 300,000 g/mol. The molecular weight can be determined using conventional Gel Permeation Chromatography (GPC).

In some embodiments, the acrylate polymer can be present in the composition in an amount ranging from about 0.25 wt % to about 10 wt %. In some embodiments, the acrylate polymer can be present in the composition in an amount of at least about 0.25 wt %; in some embodiments, at least about 0.5 wt %; in some embodiments, at least about 1 wt %, in some embodiments, at least about 1.25 wt %; in some embodiments, at least about 1.5 wt %; in some embodiments, at least about 2 wt %, in some embodiments, at least about 2.5 wt %; in some embodiments, at least about 3 wt %; and in some embodiments, at least about 3.5 wt %. In some embodiments, the acrylate polymer can be present in the composition in an amount of no greater than about 10 wt %; in some embodiments, no greater than about 8 wt %; in some embodiments, no greater than about 6 wt %; in some embodiments, no greater than about 5.5 wt %; in some embodiments, no greater than about 5 wt %; in some embodiments, no greater than about 4.5 wt %; and in some embodiments, no greater than about 4 wt %. In some embodiments, the acrylate polymer can be present in an amount of about 2 wt %. In some embodiments, the acrylate polymer can be present in any range derived from any of the endpoints listed above, such as between about 1 wt % and about 6 wt %, or between about 2 wt % and about 4 wt %, etc. At levels much above 10 wt % of acrylate polymer, the resulting composition can become sticky and unpleasant feeling.

In some embodiments, the acrylate polymer can be present in the composition as a 25% solids solution (e.g., in isopropyl palmitate, or another suitable emollient oil). In such embodiments, the 25% solids solution of acrylate polymer can be present in the composition in amount of at least about 4 wt %; in some embodiments, at least about 5 wt %; and in some embodiments, at least about 8 wt %. In some embodiments, the 25% solids solution of acrylate polymer can be present in the composition at no greater than 25 wt %; in some embodiments, no greater than about 20 wt %; in some embodiments, no greater than about 15 wt %; and in some embodiments, no greater than about 10 wt %. In some embodiments, the 25% solids solution of acrylate polymer can be present in the composition in an amount of about 8 wt %.

Note that the acrylate polymer formulations employed in the working and reference examples of the Examples section below employed 25% solids formulations (i.e., an amount listed of 8 wt % was actually 2 wt % of acrylate polymer).

In some embodiments, acrylate polymers of the present disclosure are insoluble in water and have a solubility parameter between about 6 and 10 (cal/cc)$^{1/2}$ in poorly hydrogen bonding solvents. The method for determining solubility parameter ranges of polymers and an extensive list of solvents (classified as either poorly hydrogen bonding, moderately hydrogen bonding, or strongly hydrogen bonding) are described in Polymer Handbook (edited by Bandrup and Immergut), pages IV-344-358 (1966). Acrylate polymers having the desired solubility parameter will be soluble in the oil base (e.g., the emollient oil) of the compositions. In some embodiments, the acrylate polymer may itself have emulsifying properties (i.e., those containing between 10 and 50 mole percent of acid monomers).

Silicone Resin

"Silicone resins" (or "organopolysiloxanes," or "organopolysiloxane resins") of the present disclosure include silicone-based resins having a branched, network or cage-like structure comprising polysiloxane networks.

In general, organopolysiloxanes are polymers containing siloxy units independently selected from $R_3SiO_{1/2}$ (i.e., an "M" siloxy unit), $R_2SiO_{2/2}$ (i.e., a "D" siloxy unit), $RSiO_{3/2}$ (i.e., a "T" siloxy unit), or $SiO_{4/2}$ (i.e., a "Q" siloxy unit), where R may be any organic group, and particularly, can include an alkyl, an alkylene, an alkenyl, an aryl, an aralkyl, an arylene, a hydroxyl, a hydride, or combinations thereof.

When R is a methyl group, for example, the four possible functional siloxane monomeric units can be represented as follows:

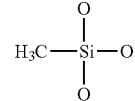

M group

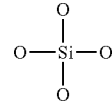

D group

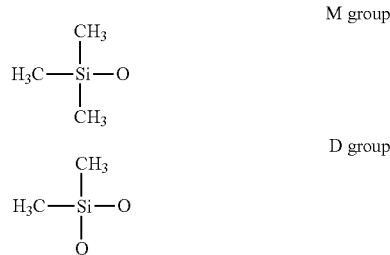

T group

Q group

These siloxy units can be combined in various manners to form silicone resins of the present disclosure that have branched, network, or cage-like structures and include at least one T and/or Q siloxy unit. The chemical and physical properties of the resulting silicone resins vary depending on the number and type of siloxy units present.

Alternatively, the formula for an organopolysiloxane may be designated by an average of the siloxy units in the organopolysiloxane as follows: $(R_nSiO_{(4-n)/2})$, where the R is independently any organic group, such as a hydrocarbon. The value of n in the average formula may be used to categorize the organopolysiloxane. For example, an average value of n=1 would indicate a predominate concentration of the T $(RSiO_{3/2})$ siloxy unit in the organopolysiloxane, while n=2 would indicate a predominance of the D $(R_2SiO_{2/2})$ siloxy unit.

A silicone resin of the present disclosure includes any organosiloxane (i.e., organopolysiloxane) containing at least one T or at least one Q siloxy unit (and in some embodiments, where the majority of the siloxy units present are T and/or Q siloxy units).

"Linear" or "cyclic" organosiloxanes containing mostly D siloxy units (i.e., silicone oils, fluids, or the like) fall outside the scope of the "silicone resins" of the present disclosure, but can be used to form silicone resins of the present disclosure. That is, the silicone resins of the present disclosure do not include linear polysiloxanes—i.e., siloxanes including mostly D siloxy units, such as polydimethylsiloxane (PDMS; also known as "dimethicone"). "Linear" organosiloxanes typically have glass transition temperatures $(T_g)$ that are lower than room temperature. In some embodiments, silicone resins of the present disclosure can include the reaction products resulting from reacting a hydroxyl endblocked "linear" organosiloxane with a "resin" organosiloxane, wherein the resin organosiloxane contains at least one $(RSiO_{3/2})$ or $(SiO_{4/2})$ siloxy unit.

The amount of each unit present in the silicone resin can be expressed as a mole fraction (i.e., a, b, c or d) of the total number of moles of all M, D, T, and Q units present in the silicone resin. Any such formula used herein to represent the silicone resin does not indicate structural ordering of the various siloxy units. Rather, such formulae are meant to provide a convenient notation to describe the relative amount of the siloxy units in the silicone resin, as per the mole fractions described above via the subscripts a, b, c or d. The mole fractions of the various siloxy units in the present organosiloxane block copolymers, as well as the silanol content, may be determined by $^{29}Si$ NMR techniques.

The silicone resin may also contain silanol groups (—SiOH). The amount of silanol groups present on the silicone resin may vary from 0.1 to 35 mole percent silanol groups. The silanol groups may be present on any siloxy units within the silicone resin.

The molecular weight and various ratios of siloxy units of the silicone resins of the present disclosure is not limiting.

The silicone resins of the present disclosure can include a variety of combinations of M, D, T, and/or Q groups. Useful classes of silicone resins for the present disclosure can include, but are not limited to, MQ resins, TD resins, and T resins. When M and Q siloxy units are predominantly used to prepare an organopolysiloxane, the resulting organosiloxane is often referred to as an "MQ resin." When T siloxy units are predominantly used to prepare an organopolysiloxane, the resulting organopolysiloxane is often referred to as a "T resin" or a "silsesquioxane resin." When T and D siloxy units are predominantly used to prepare an organopolysiloxane, the resulting organosiloxane is often referred to as a "TD resin."

"MQ resins" of the present disclosure can include any copolymeric silicone resins that comprise M and Q groups, e.g., MQ silicone resins (e.g., trialkylsiloxysilicates, such as trimethylsiloxysilicates), MQD silicone resins, and MQT silicone resins, which can have a number average molecular weight of from about 100 to about 50,000 or even from about 500 to about 20,000, and generally have methyl substituents (i.e., R is generally methyl, but need not be). The MQ silicone resins include both non-functional and functional resins, the functional resins having one or more functionalities including, for example, silicon-bonded hydrogen, silicon-bonded alkenyl and silanol.

MQ silicone resins are copolymeric silicone resins having $R_3SiO_{1/2}$ units (M units) and $SiO_{4/2}$ units (Q units). That is, MQ resins comprise clusters of quadrafunctional silicate Q groups end-capped with monofunctional trialkylsiloxy M groups. Such resins are described in, for example, Encyclopedia of Polymer Science and Engineering, vol. 15, John Wiley & Sons, New York, (1989), pp. 265 to 270, and U.S. Pat. Nos. 2,676,182; 3,627,851; 3,772,247; and 5,248,739. MQ silicone resins having functional groups are described in U.S. Pat. No. 4,774,310, which describes silyl hydride groups, U.S. Pat. No. 5,262,558, which describes vinyl and trifluoropropyl groups, and U.S. Pat. No. 4,707,531, which describes silyl hydride and vinyl groups, each of which is incorporated herein by reference. The above-described resins are generally prepared in solvent. Dried or solventless MQ silicone resins are prepared as described in U.S. Pat. Nos. 5,319,040, 5,302,685 and 4,935,484, each of which is incorporated herein by reference.

MQD silicone resins are terpolymers having $R_3SiO_{1/2}$ units (M units), $SiO_{4/2}$ units (Q units), and $R_2SiO_{2/2}$ units (D units), as described, e.g., in U.S. Pat. No. 5,110,890 (incorporated by reference herein) and Japanese Kokai HEI 2-36234.

MQT silicone resins are terpolymers having $R_3SiO_{1/2}$ units (M units), $SiO_{4/2}$ units (Q units), and $RSiO_{3/2}$ units (T units).

Commercially available MQ resins include SR-545 MQ resin in toluene available from General Electric Co., Silicone Resins Division (Waterford, N.Y.), MQOH resins which are MQ silicone resins in toluene available from PCR, Inc. (Gainesville, Fla.). Such resins are generally supplied in organic solvent. These organic solutions of MQ silicone resin may be used as-is or may be dried by any number of techniques known in the art including, e.g., spray drying, oven drying, and steam separation, to provide a MQ silicone resin at 100 percent non-volatile content. The MQ silicone resin can also include blends of two or more silicone resins.

Particularly suitable MQ resins for compositions of the present disclosure include alkylsiloxysilicates, such as trialkylsiloxysilicates (e.g., trimethylsiloxysilicates). For example, as detailed in the Examples section below, useful trimethylsiloxysilicates are available under the trade designation "MQ 1600 solid resin" (or the trade designation "TI-7012 solid resin"—healthcare grade) from Dow Corning Corporation, Midland, Mich.

TD resins of the present disclosure can include any copolymeric silicone resins that comprise (or predominantly comprise) T and D groups. The R group in TD resins is generally a methyl or a hexyl group.

T resins of the present disclosure can include any silicone resin comprising (or predominantly comprising) T groups, which are often referred to as silsesquioxanes. Particularly suitable T resins for compositions of the present disclosure include alkylsilsesquioxanes, such as alkylsilsesquioxanes (e.g., propylsilsesquioxanes) and arylsilsesquioxanes (e.g., phenylsilsesquioxanes). For example, as detailed in the Examples section below, a useful polypropylsilsesquioxane is available under the trade designation "MQ 1640 flake resin" from Dow Corning Corporation, Midland, Mich.

T resins are generally characterized by the empirical chemical formula $RSiO_{3/2}$ and a cage-like structure, which can be in the general structure of a cube, a hexagonal prism, an octagonal prism, a decagonal prism, a dodecagonal prism, or another suitable three-dimensional structure.

Other useful silicone resins for compositions of the present disclosure include a trimethylsiloxysilicate resin (TMS), available under the trade designation "Belsil Silicone Resins TMS 803," from Wacker Chemical Corporation; a TMS available under the trade designation "BRB—TMS," "BRB—TMS 30D" (i.e., 30% TMS in dimethicone), or "BRB—TMS 50D" (i.e., 50% TMS in cyclopentasiloxane) from BRB International; a polyphenylsilsequioxane, available under the trade designation "Belsil Silicone Resins SPR 45 VP" from Wacker Chemical Corporation; a cyclopentasiloxane and polypropylsilsesquioxane, available under the trade designation "670 Silicone Fluid" from Dow Corning; or combinations thereof.

Silicone resins of the present disclosure can also include silicone resins comprising metals, e.g., aluminosilicates, borosilicates, and combinations thereof.

The silicone resins of the present disclosure can have a variety of shapes or structures, including, but not limited to, flake, rod, sphere, porous, other suitable shapes or structures, or combinations thereof.

In some embodiments, the silicone resin can be present in the composition in an amount ranging from about 0.25 wt % to about 15 wt %. In some embodiments, the silicone resin can be present in the composition in an amount of at least about 0.25 wt %; in some embodiments, at least about 0.5 wt %; in some embodiments, at least about 1 wt %, in some embodiments, at least about 1.25 wt %; in some embodiments, at least about 1.5 wt %; in some embodiments, at least about 2 wt %; in some embodiments, at least about 2.5 wt %; in some embodiments, at least about 3 wt %; and in some embodiments, at least about 3.5 wt %. In some embodiments, the silicone resin can be present in the composition in an amount of no greater than about 15 wt %; in some embodiments, no greater than about 10 wt %; in some embodiments, no greater than about 8 wt %; in some embodiments, no greater than about 5 wt %; in some embodiments, no greater than about 4.5 wt %; and in some embodiments, no greater than about 4 wt %. In some embodiments, the silicone resin can be present in an amount of about 2 wt %. In some embodiments, the silicone resin can be present in any range derived from any of the endpoints listed above, such as between about 0.5 wt % and about 3 wt %, or between about 1 wt % and about 2 wt %, etc.

Emollient Oil

The oil carrying the acrylate polymer may be any oil or mixture of oils, such as those conventionally used in the cosmetic art. The oil base of the compositions may be solid or liquid, but the entire formulation should be somewhat fluid at skin temperatures for ease of application. Examples of suitable oils include, but are not limited to, saturated fatty esters and diesters such as isopropyl palmitate, cetyl palmitate, isopropyl myristate, butyl stearate, diisopropyl adipate, dicapryl adipate, dioctyl sebacate, propylene glycol dipelargonate, etc.; paraffin oils and waxes; mineral oil; animal and vegetable oils, including mink oil, coconut oil and derivatives thereof, palm oil, corn oil, cocoa butter, sesame oil, and the like; lanolin derivatives; fatty alcohols, such as isostearyl alcohol, isocetyl alcohol, and straight chain alcohols from $C_6$-$C_{18}$; petrolatum, and any suitable petroleum distillates which are toxicologically safe such as $C_8$-$C_{18}$ isoparaffin hydrocarbon solvents; cetyl/stearyl alcohol; silicone fluids/oils; propoxylate of stearyl alcohol (e.g., 15 mole); propoxylate of myristyl propionate (e.g., 2 mole); "PPG-15 stearyl ether," commercially available from Croda USA, Newcastle Del. and combinations thereof.

Particularly useful emollient oils can include, but are not limited to, isopropyl palmitate, coconut oil, mineral oil, PPG 15 stearyl ether, dicapryl adipate, paraffin wax, or combinations thereof.

The oils mentioned above are included by way of example only and are not intended to be limiting. In general, any nonvolatile material, or mixture of materials, which is toxicologically safe for human use and which has a solubility parameter between about 6 and 10 $(cal/cc)^{1/2}$ in poorly hydrogen bonding solvents may be used as the emollient oil in the compositions of the present disclosure.

In some embodiments, the total amount of emollient oil(s) present in the composition can range from about 5 wt % to about 50 wt %. In some embodiments, the total amount of emollient oil(s) present in the composition can be at least about 5 wt %; in some embodiments, at least about 10 wt %; in some embodiments, at least about 12 wt %; in some embodiments, at least about 15 wt %, in some embodiments, at least about 20 wt %; and in some embodiments, at least about 25 wt %. In some embodiments, the total amount of emollient oil(s) present in the composition can be no greater than about 50 wt %; in some embodiments, no greater than about 45 wt %; in some embodiments, no greater than about 40 wt %; in some embodiments, no greater than about 35 wt %; and in some embodiments, no greater than about 30 wt %. In some embodiments, the total amount of emollient oil(s) is present in the composition in any range derived from any of the endpoints listed above, such as between about 20 wt % and about 40 wt %, or between about 25 wt % and about 35 wt %, etc.

Methods of Use

Some aspects of the present disclosure can provide methods of using the compositions of the present disclosure, e.g., for moisturizing mammalian skin. Such methods can include coating the skin with the composition. In some embodiments, the present disclosure can provide methods of moisturizing mammalian skin without adversely affecting the adhesion of an acrylate or rubber based pressure-sensitive adhesive. Such methods can include coating the skin with the composition, and applying a pressure-sensitive adhesive (e.g., an acrylate or rubber based pressure-sensitive adhesive) over the composition. The pressure-sensitive adhesive can be provided by, or form a portion of, a tape, a dressing, or the like. In some embodiments, the composition can be formulated such that the pressure-sensitive adhesive adheres at least as well and, in some cases, more strongly to treated skin than to untreated skin. In some embodiments, the composition can be formulated such that the adhesion of the pressure-sensitive adhesive to the composition is greater than the adhesion of the pressure-sensitive adhesive to skin treated (e.g., coated) with the emollient oil alone.

Composite Structures

Some aspects of the present disclosure can provide a composite structure applied to mammalian skin. Such a composite structure can include a coating applied to the skin comprising a composition (e.g., a dried form thereof) of the present disclosure; and a pressure-sensitive adhesive (e.g., an acrylate or rubber based pressure-sensitive adhesive) applied over the coating. The pressure-sensitive adhesive can be provided by, or form a portion of, a tape, a dressing, or the like. In some embodiments, the composition can be formulated such that the pressure-sensitive adhesive adheres at least as well and, in some cases, more strongly to treated skin than to untreated skin. In some embodiments, the composition can be formulated such that the adhesion of the pressure-sensitive adhesive to the skin coated with the coating is greater than the adhesion of the pressure-sensitive adhesive to skin coated with the emollient oil alone.

The following embodiments are intended to be illustrative of the present disclosure and not limiting.

EMBODIMENTS

Embodiment 1

A composition for application to mammalian skin, the composition comprising:
an emulsion comprising:
an oil phase comprising:
(a) an acrylate polymer in an amount of from about 0.25 wt % to about 10 wt %, and
(b) a silicone resin in an amount of from about 0.5 wt % to about 15 wt %;
wherein (a) and (b) are dissolved in a non-volatile emollient oil.

Embodiment 2

The composition of embodiment 1, wherein the emulsion is a water-in-oil emulsion.

Embodiment 3

The composition of embodiment 1 or 2, wherein the composition is essentially free of any additional emulsifiers.

Embodiment 4

The composition of any of embodiments 1-3, wherein the composition is configured to dry to a coating comprising at least 60 wt % of the emollient oil.

Embodiment 5

The composition of any of embodiments 1-4, wherein the composition exhibits a barrier durability of at least 35% after at least two simulated incontinence episodes.

Embodiment 6

The composition of any of embodiments 1-5, wherein the composition exhibits a barrier durability of at least 40% after at least two simulated incontinence episodes.

Embodiment 7

The composition of any of embodiments 1-6, wherein the acrylate polymer is derived from the polymerization of at least one ester monomer and at least one acid monomer.

Embodiment 8

The composition of embodiment 7, wherein the at least one ester monomer is selected from the same or different monomers of Formula I:

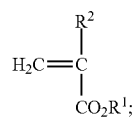

and
wherein the at least one acid monomer is selected from the same or different monomers of Formula II:

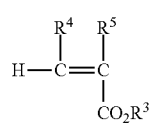

Embodiment 9

The composition of embodiment 7 or 8, wherein the acrylate polymer is derived from polymerization of a mixture of from 40 to 95 mole percent of the at least one ester monomer and from 5 to 60 mole percent of the at least one acid monomer.

Embodiment 10

The composition of embodiment 9, wherein the at least one acid monomer is present in an amount of from 10 to 50 mole percent.

Embodiment 11

The composition of any of embodiments 7-10, wherein the at least one ester monomer comprises an alkyl ester of acrylic, methacrylic, itaconic or maleic acid, wherein the ester alkyl group includes 1 to 18 carbon atoms.

Embodiment 12

The composition of any of embodiments 7-11, wherein the at least one acid monomer comprises an unesterified α,β-olefinically unsaturated carboxylic acid.

Embodiment 13

The composition of any of embodiments 1-12, wherein the acrylate polymer is a terpolymer derived from isooctyl acrylate, stearyl methacrylate, and acrylic acid.

Embodiment 14

The composition of any of embodiments 1-13, wherein the terpolymer is derived from a mixture comprising at least 50 mole percent isooctyl acrylate, at least 40 mole percent stearyl methacrylate, and at least 5 mole percent acrylic acid.

Embodiment 15

The composition of any of embodiments 1-14, wherein the acrylate polymer has a solubility parameter of about 6 to about 10 $(cal/cc)^{1/2}$ in poorly hydrogen bonding solvents.

Embodiment 16

The composition of any of embodiments 1-15, wherein the acrylate polymer is present in the composition in an amount ranging from about 1 wt % to about 6 wt %.

Embodiment 17

The composition of any of embodiments 1-16, wherein the acrylate polymer is present in the composition in an amount ranging from about 1 wt % to about 5 wt %.

Embodiment 18

The composition of any of embodiments 1-17, wherein the acrylate polymer is present in the composition in an amount ranging from about 1 wt % to about 3 wt %.

Embodiment 19

The composition of any of embodiments 1-18, wherein the silicone resin comprises a flaked resin.

Embodiment 20

The composition of any of embodiments 1-19, wherein the silicone resin comprises at least one T siloxy unit or at least one Q siloxy units.

Embodiment 21

The composition of any of embodiments 1-20, wherein the silicone resin comprises at least one of an MQ resin, a T resin, and a TD resin.

Embodiment 22

The composition of any of embodiments 1-21, wherein the silicone resin comprises an MQ resin.

Embodiment 23

The composition of any of embodiments 1-22, wherein the silicone resin comprises a T resin.

Embodiment 24

The composition of any of embodiments 1-23, wherein the silicone resin comprises a TD resin.

Embodiment 25

The composition of any of embodiments 1-24, wherein the silicone resin comprises a flaked MQ resin.

Embodiment 26

The composition of any of embodiments 1-25, wherein the silicone resin comprises an organopolysiloxane resin network.

Embodiment 27

The composition of any of embodiments 1-26, wherein the silicone resin comprises at least one of an alkylsiloxysilicate and an alkylsilsesquioxane.

Embodiment 28

The composition of any of embodiments 1-27, wherein the silicone resin comprises a trimethylsiloxysilicate.

Embodiment 29

The composition of any of embodiments 1-28, wherein the silicone resin comprises at least one of a trimethylsiloxysilicate and a polypropylsilsesquioxane.

Embodiment 30

The composition of any of embodiments 1-29, wherein the silicone resin is present in the composition in an amount ranging from about 0.5 wt % to about 3 wt %.

Embodiment 31

The composition of any of embodiments 1-30, wherein the silicone resin is present in the composition in an amount ranging from about 1 wt % to about 2 wt %.

Embodiment 32

The composition of any of embodiments 1-31, wherein the composition comprises a water phase present in the composition in an amount ranging from about 35 wt % to about 90 wt %.

Embodiment 33

The composition of any of embodiments 1-32, wherein the composition is essentially free of any ethylene acrylic acid copolymers.

Embodiment 34

The composition of any of embodiments 1-33, wherein the composition has a viscosity ranging from about 5 Pa·s to about 250 Pa·s.

Embodiment 35

The composition of any of embodiments 1-34, wherein the composition has a viscosity ranging from about 7 Pa·s to about 200 Pa·s.

Embodiment 36

The composition of any of embodiments 1-35, wherein the composition has a viscosity ranging from about 10 Pa·s to about 150 Pa·s.

Embodiment 37

The composition of any of embodiments 1-36, wherein the emollient oil has a solubility parameter of about 6 to about 10 $(cal/cc)^{1/2}$ in poorly hydrogen bonding solvents.

Embodiment 38

The composition of any of embodiments 1-37, wherein the emollient oil comprises at least one of isopropyl palmitate, coconut oil, mineral oil, PPG 15 stearyl ether, dicapryl adipate, paraffin wax, and a combination thereof.

Embodiment 39

A composite structure applied to mammalian skin, the composite structure comprising:
  a coating applied to the skin comprising the composition of any of the preceding embodiments; and
  an acrylate or rubber based pressure-sensitive adhesive applied over the coating;
  wherein the composition is formulated such that the adhesion of the pressure-sensitive adhesive to the skin coated with the coating is greater than the adhesion of the pressure-sensitive adhesive to skin coated with the emollient oil alone.

Embodiment 40

A composite structure applied to mammalian skin, the composite structure comprising:
  a coating applied to the skin comprising the composition of any of the preceding embodiments; and
  an acrylate or rubber based pressure-sensitive adhesive applied over the coating;
  wherein the composition is formulated such that the adhesion of the pressure-sensitive adhesive to the skin coated with the coating is at least as great as the adhesion of the pressure-sensitive adhesive to untreated skin.

Embodiment 41

A method of moisturizing mammalian skin, the method comprising:
  coating the skin with the composition of any of the preceding embodiments; and
  applying an acrylate or rubber based pressure-sensitive adhesive over the composition;
  wherein the composition is formulated such that the adhesion of the pressure-sensitive adhesive to the composition is greater than the adhesion of the pressure-sensitive adhesive to skin coated with the emollient oil alone.

Embodiment 42

A method of moisturizing mammalian skin, the method comprising:
coating the skin with the composition of any of the preceding embodiments; and
applying an acrylate or rubber based pressure-sensitive adhesive over the composition;
wherein the composition is formulated such that the adhesion of the pressure-sensitive adhesive to the skin coated with the coating is at least as great as the adhesion of the pressure-sensitive adhesive to untreated skin.

The following working examples are intended to be illustrative of the present disclosure and not limiting.

EXAMPLES

Materials

"MQ-1600": Trimethylsiloxysilicate resin, available from Dow Corning, also available under the trade designation "TI-7012 solid resin" or "MQ 1600 solid resin"
"MQ-1640": Trimethylsiloxysilicate and Polypropyl silsesquioxane, available from Dow Corning under the trade designation "MQ-1640 flake resin"
"Acrylate polymer": Terpolymer acrylate, prepared according to U.S. Pat. No. 6,200,596, Example 5
"POLYDERM PPI POLYMER": Polydiethylene Glycol Adipate/IPDI, available from Alzo International Inc., UK under the trade designation "POLYDERM PPI-PE, INCI"
"GIOVAREX BTB-50": Isododecane (and) Behenyl Methacrylate/t-Butyl Methacrylate Copolymer, available from Phoenix Chemical Inc., Sommerville, US under the trade designation "GIOVAREX BTB-50, INCI"
"INTELIMER 8600": C8-22 Alkyl Acrylates/Methacrylic Acid Crosspolymer, available from Air Products under the trade designation "INTELIMER 8600"
"Cithrol DPHS Surfactant": surfactant available from Croda, East Yorkshire, UK under the trade designation "CITHROL DPHS"

Sample Preparation and Test Methods
Test Sample Preparation

The ability of water-in-oil emulsions according to the present disclosure to provide a durable skin protection was tested on pig skin samples obtainable from any local meat food supplier. After removal of the pig skin samples from the refrigerator, the samples were allowed to equilibrate to room temperature for 30 min. During this time, the pig skin samples were prepared by removing excess subcutaneous fat layers from the rear of each sample. This helped to ensure that the pig skin lied flat during testing. The pig skin samples were cut into a size of 2 cm×2 cm. In order to standardize the pig skin as much as possible, the pig skin was wiped with a piece of tissue paper soaked in isopropyl alcohol (IPA) for a total of four times to remove natural oils and contaminants from the surface.

FTIR Pig Skin Test Method

FTIR was used to measure barrier durability while simulating the effect of repeated Simulated Incontinence Episodes (SIE). The FTIR method was conducted according to the following protocol:

1. Using the ATR FTIR (Thermo Scientific Nicolet IS5) with the ID5 probe, an FTIR spectrum was taken of each pig skin sample to provide an "initial" baseline FTIR spectrum.
2. 30 mg test emulsion was applied to the skin sample (2 cm×2 cm) and allowed to dry for 2 hours.
3. Using the ATR FTIR with the ID5 probe, each sample was analyzed again to provide a "post cream" FTIR spectrum.
4. A wet paper towel (approximately 5 cm×5 cm), saturated to hold its own water, was applied to each skin sample to simulate an incontinence episode (SIE). The wet towel was left in place for 10 min.
5. After removal of the wet paper towel, the sample was immediately analyzed using the ATR FTIR ID5 probe. This provided a "Simulated Incontinence Episode 1" (SIE 1) FTIR spectrum.
6. To simulate cleansing after the SIE, each sample was wiped with a clean dry paper towel to which a small amount of TENA 3 in 1 Wash Mousse (available from SCA Hygiene Products, Gotenburg, Sweden) was applied. Five gentle wipes in one direction were done, then 5 more at 90 degrees to the first direction. This was repeated twice using no cleansing foam.

Steps 4 to 6 were repeated to obtain 2 SIE cycles and accordingly 2 SIE FTIR spectra. Each test was replicated three times and the mean values calculated. The results of the generated spectra were analyzed as given below.

Analysis of FTIR Spectra for Barrier Durability

The barrier durability was analyzed by the Omnic Software program (available from Thermo Scientific), calculating the absorbance ratio of the peak area to the area under the baseline at 2800-3000 $cm^{-1}$ (thus removing variability from sample contact with the ATR crystal). The percent remaining emulsion was calculated from the data obtained for post cream (100%) and the data obtained after the simulated incontinence episodes indicated as 'SIE 1' and 'SIE 2'. The difference between these values indicates how much of the applied emulsion was removed. Smaller difference represents less removal or higher durability of the emulsion. It should be noted that the use of a biological substrate produces variance, and while measures were taken to ensure this variability was kept to a minimum, some natural variability is present in the data provided.

Preparation of the Emulsions

Water-in-oil emulsions were prepared according to the general method as outlined for example 1 below. Some of the ingredients were added to all of the examples, reference examples and comparative examples in the same amount. These ingredients (further referred to as 'OTHER ADDITIVES') and their amount used is listed in Table 1.

TABLE 1

| composition and amount of 'OTHER ADDITIVES' | | |
|---|---|---|
| Designator 'other additives' | Availability | Amount (parts by weight) |
| COCONUT OIL | Columbus Vegetable Oils, IL, USA | 9.35 |
| LIGHT MINERAL OIL | Tennants Ltd, Manchester | 3.94 |
| DICAPRYL ADIPATE | Aston Chemicals, Buckinghamshire, UK | 4.00 |
| PPG 15 STEARYL ETHER | Croda, DE, USA | 7.32 |
| PARAFFIN WAX | Safic Alcan, Birchwood, Warrington, UK | 4.83 |
| GLYCEROL | Univar, Bradford, UK | 6.00 |
| MAGNESIUM SULPHATE HEPTAHYDRATE | Avantor, Deventer, Netherlands | 0.50 |
| DEKABEN PBH | IMCD, Sutton, UK | 1.00 |
| DIMETHICONE | Azelis, Hertford, UK | 1.30 |
| Total 'OTHER ADDITIVES' | | 38.24 |

Examples 1 to 5 and Comparative Example C-1

The water-in-oil emulsion of Example 1 was prepared as follows:

The oil phase was prepared by mixing following ingredients: acrylate polymer (8 parts of a 25% solids solution of acrylate polymer in isopropyl palmitate (IPP), prepared according to U.S. Pat. No. 6,200,596 Example 5), light mineral oil (3.94 parts), Coconut oil (9.35 parts), "PPG-15 Stearyl ether" (7.32 parts), dicapryl adipate (4 parts), MQ-1600 (i.e., the silicone resin; 2 parts) and paraffin wax (4.83 parts). The water phase was prepared by mixing following ingredients: deionized water (51.76 parts), magnesium sulphate heptahydrate (0.50 parts), glycerol (6 parts), and Dekaben PBH preservative (1 part). The water-in-oil formulation was prepared by heating the oil phase and the water phase in separate vessels, to approximately 70° C. with slow agitation (about 75 rpm using a hot plate stirrer). Then, the water phase was added to the oil phase with rapid agitation (about 4000 rpm using a Silverson Homogenizer). Then, dimethicone (1.3 parts) was added to the mixture and the resulting mixture was homogenized while cooling to 30° C. to produce a stable emulsion.

The water-in-oil emulsions of Examples 2 to 5 were prepared according to the procedure as given above for Example 1 but with the ingredients as listed in Table 2. In all cases, stable emulsions were obtained without additional emulsifier or surfactant. Comparative Example C-1 was made with 3M Cavilon Durable Barrier Cream 3391 (commercially available from 3M Company, St. Paul, Minn.).

TABLE 2

Composition of water-in-oil emulsions used in Examples (Ex) 1 to 5

| Ingredients (parts by weight) | Ex 1 | Ex 2 | Ex 3 | Ex 4 | Ex 5 |
|---|---|---|---|---|---|
| Acrylate Polymer (25% solids solution) | 4.00 | 15.00 | 4.00 | 15.00 | 8.00 |
| Silicone Resin (MQ1600 solid resin) | 0.50 | 0.50 | 10.00 | 10.00 | 2.00 |
| Purified Water | 57.26 | 50.76 | 47.76 | 36.76 | 51.76 |
| Other additives | 38.24 | 38.24 | 38.24 | 38.24 | 38.24 |
| Total | 100.00 | 100.00 | 100.00 | 100.00 | 100.00 |

The emulsions of Examples 1 to 5 and Comparative Example C-1 were analyzed for barrier durability using the FTIR analysis method as given above. The percent remaining cream after each simulated incontinence episode (SIE) is listed in Table 3.

TABLE 3

Barrier durability of the emulsions from Examples 1 to 5 and Comparative Example C-1

| % Cream Remaining | Example 1 | Example 2 | Example 3 | Example 4 | Example 5 | C-1 |
|---|---|---|---|---|---|---|
| Post Cream | 100.00 | 100.00 | 100.00 | 100.00 | 100.00 | 100.00 |
| SIE 1 | 80.31 | 100.05 | 102.35 | 95.82 | 85.14 | 88.95 |
| SIE 2 | 55.61 | 98.79 | 42.52 | 72.74 | 97.17 | 81.11 |

Examples 6 to 10

The water-in-oil emulsions of Examples 6 to 10 were prepared according to the procedure as given above for Example 1 and with the ingredients as listed in Table 4.

TABLE 4

Composition of water-in-oil emulsions used in Examples (Ex) 6 to 10

| Ingredients (parts by weight) | Ex 6 | Ex 7 | Ex 8 | Ex 9 | Ex 10 |
|---|---|---|---|---|---|
| Acrylate Polymer (25% solids solution) | 4.00 | 15.00 | 4.00 | 15.00 | 8.00 |
| Silicone Resin (MQ1640 flake resin) | 0.50 | 0.50 | 10.00 | 10.00 | 2.00 |
| Purified Water | 57.26 | 46.26 | 47.76 | 36.76 | 51.76 |
| Other additives | 38.24 | 38.24 | 38.24 | 38.24 | 38.24 |
| Total | 100.00 | 100.00 | 100.00 | 100.00 | 100.00 |

The emulsions of Examples 6 to 10 were analyzed for barrier durability using the FTIR analysis method as given above. The percent of emulsion (cream) remaining after each simulated incontinence episode (SIE) is listed in Table 5.

TABLE 5

Barrier durability of the emulsions from Examples 6 to 10

| % Cream remaining | Example 6 | Example 7 | Example 8 | Example 9 | Example 10 |
|---|---|---|---|---|---|
| Post Cream | 100.00 | 100.00 | 100.00 | 100.00 | 100.00 |
| SIE 1 | 77.12 | 85.34 | 102.32 | 91.79 | 110.06 |
| SIE 2 | 43.07 | 75.31 | 77.77 | 82.56 | 78.50 |

Comparative Examples C-2 to C-4

The water-in-oil emulsions of Comparative Examples C-2 to C-4 were prepared according to the procedure as given above for Example 1 and with the ingredients as listed in Table 6. Contrary to the stable water-in-oil emulsions of Examples 1 to 12, no stable emulsions could be made in Comparative Examples C-2 to C-4, where the acrylate polymer was replaced with commercially available polymers that are useful in cosmetic compositions.

TABLE 6

Composition of water-in-oil emulsions of Comparative Examples C-2 to C-4

| Ingredients (parts by weight) | C-2 | C-3 | C-4 |
|---|---|---|---|
| Acrylate Polymer (25% solids solution) | / | / | / |
| GIOVAREX BTB-50 | 8.00 | / | / |
| POLYDERM PPI POLYMER | / | 8.00 | / |
| INTELIMER 8600 | / | / | 8.00 |
| Silicone Resin (MQ 1600 Solid resin) | 2.00 | 2.00 | 2.00 |
| Purified Water | 51.76 | 51.76 | 51.76 |
| Other additives | 38.24 | 38.24 | 38.24 |
| Total | 100.00 | 100.00 | 100.00 |

Example 13

In Example 13, the water-in-oil emulsion of Example 6 was tested for the ability to influence tape adhesion to the skin. Therefore, 30 mg of the water-in-oil emulsion of Example 6 was applied to a pig skin sample and allowed to dry for 1 hour. Pressure-sensitive adhesive strips or tapes available under the trade designations "3M MICROPORE TAPE", "3M KIND REMOVAL SILICONE TAPE", AND "3M MEDIPORE TAPE" from 3M Company (St. Paul, Minn.); as well as a dressing available under the trade designation "3M TEGADERM FILM" (3M Company) were applied to both treated (i.e., with the water-in-oil emulsion of Example 6) and untreated skin samples. After 30 min., the tapes were manually removed. It was observed that the water-in-oil emulsion of Example 6 did not adversely affect the tape adhesion of any of the tapes tested. That is, the adhesion of the tapes/dressing to the skin treated with the composition of Example 6 was at least as great as the adhesion of the tapes/dressing to the untreated skin. All tapes remained in place for the duration of the testing. It was further observed that the water-in-oil emulsion of Example 6 did not appear to increase tape adhesion with time.

All references and publications cited herein are expressly incorporated herein by reference in their entirety into this disclosure.

Various features and aspects of the present disclosure are set forth in the following claims.

What is claimed is:

1. A composition for application to mammalian skin, the composition comprising:
   an emulsion comprising:
   an oil phase comprising:
   (a) an acrylate polymer in an amount of from about 0.25 wt % to about 10 wt % of the composition, and
   (b) a silicone resin in an amount of from about 0.5 wt % to about 15 wt % of the composition;
   wherein (a) and (b) are dissolved in a non-volatile emollient oil.

2. The composition of claim 1, wherein the emulsion is a water-in-oil emulsion.

3. The composition of claim 1, wherein the composition is essentially free of any additional emulsifiers.

4. The composition of claim 1, wherein the composition is configured to dry to a coating comprising at least 60 wt % of the emollient oil.

5. The composition of claim 1, wherein the composition exhibits a barrier durability of at least 35% after at least two simulated incontinence episodes.

6. The composition of claim 1, wherein the acrylate polymer is derived from the polymerization of at least one ester monomer and at least one acid monomer.

7. The composition of claim 6, wherein the at least one ester monomer is selected from the same or different monomers of Formula I:

where
R$^1$ is an alkyl radical containing 4 to 18 carbon atoms in cyclic, straight- or branched-chain configuration, and
R$^2$ is hydrogen or an alkyl radical containing one to four carbon atoms; and
wherein the at least one acid monomer is selected from the same or different monomers of Formula II:

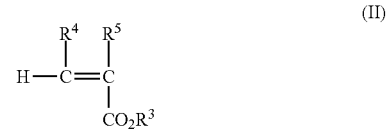

where
R$^3$ is hydrogen (H) or an alkyl group containing 1 to 18 carbon atoms;
R$^4$ is hydrogen (H), methyl (—CH$_3$), or —CO$_2$R$^3$, and
R$^5$ is hydrogen (—H), a lower alkyl or —CH$_2$CO$_2$R$^3$, provided that when R$^4$ is not hydrogen, R$^5$ is hydrogen and when R$^5$ is not hydrogen, R$^4$ is hydrogen, and further provided that at least one R$^3$ is hydrogen.

8. The composition of claim 7, wherein the at least one ester monomer comprises an alkyl ester of acrylic, methacrylic, itaconic or maleic acid, wherein the ester alkyl group includes 1 to 18 carbon atoms.

9. The composition of claim 7, wherein the at least one acid monomer comprises an unesterified α,β-olefinically unsaturated carboxylic acid.

10. The composition of claim 7, wherein the acrylate polymer is a terpolymer derived from isooctyl acrylate, stearyl methacrylate, and acrylic acid.

11. The composition of claim 1, wherein the acrylate polymer is present in the composition in an amount ranging from about 1 wt % to about 6 wt %.

12. The composition of claim 1, wherein the acrylate polymer is present in the composition in an amount ranging from about 1 wt % to about 3 wt %.

13. The composition of claim 1, wherein the silicone resin comprises at least one T siloxy unit or at least one Q siloxy units.

14. The composition of claim 1, wherein the silicone resin comprises at least one of an MQ resin, a T resin, and a TD resin.

15. The composition of claim 1, wherein the silicone resin comprises at least one of an alkylsiloxysilicate and an alkylsilsesquioxane.

16. The composition of claim 1, wherein the silicone resin is present in the composition in an amount ranging from about 0.5 wt % to about 3 wt %.

17. The composition of claim 1, wherein the composition comprises a water phase present in the composition in an amount ranging from about 35 wt % to about 90 wt %.

18. The composition of claim 1, wherein the composition has a viscosity ranging from about 5 Pa·s to about 250 Pa·s.

19. The composition of claim 1, wherein the emollient oil comprises at least one of isopropyl palmitate, coconut oil, mineral oil, polypropylene glycol (15) stearyl ether, dicapryl adipate, paraffin wax, and a combination thereof.

* * * * *

UNITED STATES PATENT AND TRADEMARK OFFICE
CERTIFICATE OF CORRECTION

PATENT NO. : 10,028,896 B2
APPLICATION NO. : 15/312108
DATED : July 24, 2018
INVENTOR(S) : Andrew Henry Page 1 of 1

It is certified that error appears in the above-identified patent and that said Letters Patent is hereby corrected as shown below:

In the Specification

Column 8
Line 42          Delete "(MO" and insert -- $(M_n)$ --, therefor.

In the Claims

Column 24
Line 36          In Claim 7, delete "(H)" and insert -- (—H) --, therefor.
Line 38          In Claim 7, delete "(H)," and insert -- (—H), --, therefor.

Signed and Sealed this
Twenty-eighth Day of August, 2018

Andrei Iancu
*Director of the United States Patent and Trademark Office*